US009504177B2

(12) United States Patent
Shah et al.

(10) Patent No.: US 9,504,177 B2
(45) Date of Patent: Nov. 22, 2016

(54) HERMETIC ELECTRONICS PACKAGE WITH DUAL-SIDED ELECTRICAL FEEDTHROUGH CONFIGURATION

(75) Inventors: Kedar G. Shah, Oakland, CA (US); Satinderpall S. Pannu, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 300 days.

(21) Appl. No.: 14/118,192

(22) PCT Filed: Jun. 14, 2012

(86) PCT No.: PCT/US2012/042540
§ 371 (c)(1), (2), (4) Date: Jul. 29, 2014

(87) PCT Pub. No.: WO2012/174300
PCT Pub. Date: Dec. 20, 2012

(65) Prior Publication Data
US 2014/0347839 A1 Nov. 27, 2014

Related U.S. Application Data

(60) Provisional application No. 61/496,846, filed on Jun. 14, 2011.

(51) Int. Cl.
*H05K 1/03* (2006.01)
*H05K 5/06* (2006.01)
(Continued)

(52) U.S. Cl.
CPC ........... *H05K 5/069* (2013.01); *A61B 5/04001* (2013.01); *A61B 5/6861* (2013.01);
(Continued)

(58) Field of Classification Search
CPC ........ H05K 5/06; H05K 5/0247; H05K 5/00; H05K 5/0095; H05K 5/02; H05K 1/0224; H05K 2201/0707; H05K 2201/10371; H05K 9/0022; H05K 9/0024; H05K 9/0052; H05K 1/0218; A61N 1/3754; A61N 1/0543; A61N 1/05; A61N 1/0502; A61N 1/0504; H02G 3/08; B60R 16/0239; H01L 23/10; H01L 23/045; H01L 23/055; H01L 2224/1302; H01L 2224/141; H01L 2224/161; H01L 2224/171; H01L 2224/211; H01L 2224/221; H01L 2224/2902; H01L 2224/301; H01L 2224/321; H01L 2224/331; H01L 2224/3702; H01L 2224/401; H01L 2224/411; H01L 2224/4502; H01L 2224/481; H01L 2224/491; H01L 23/49838; H01L 23/22; H01L 23/24; H01L 2225/06548; H01L 2225/1047; H01L 23/043; H01L 23/3128; H01L 25/10; H01L 25/117; H01J 5/32; H01B 17/303
USPC ........ 607/116; 257/787, 687, 692, 685, 699, 257/686; 361/816, 818; 174/520, 50.59
See application file for complete search history.

(56) References Cited

U.S. PATENT DOCUMENTS 7,045,885 B1 * 5/2006 Chen ........................ H01L 23/26 257/678
7,818,876 B2 * 10/2010 Suaning ............... A61N 1/3754 29/825

(Continued)

FOREIGN PATENT DOCUMENTS

EP 1 308 762 A1 7/2003
KR 1006191030000 9/2006

*Primary Examiner* — Angel R Estrada
*Assistant Examiner* — Pete Lee
(74) *Attorney, Agent, or Firm* — James S. Tak

(57) ABSTRACT

A hermetic electronics package includes a metal case with opposing first and second open ends, with each end connected to a first feedthrough construction and a second feedthrough construction. Each feedthrough contruction has an electrically insulating substrate and an array of electrically conductive feedthroughs extending therethrough, with the electrically insulating substrates connected to the opposing first and second open ends, respectively, of the metal case so as to form a hermetically sealed enclosure. A set of electronic components are located within the hermetically sealed enclosure and are operably connected to the feedthroughs of the first and second feedthrough constructions so as to electrically communicate outside the package from opposite sides of the package.

12 Claims, 8 Drawing Sheets

(51) Int. Cl.

| | |
|---|---|
| ***A61B 5/00*** | (2006.01) |
| ***A61B 5/04*** | (2006.01) |
| ***A61N 1/375*** | (2006.01) |
| ***H02G 3/00*** | (2006.01) |
| ***H05K 3/46*** | (2006.01) |
| ***H05K 5/02*** | (2006.01) |
| *H01L 23/00* | (2006.01) |
| *H01L 23/498* | (2006.01) |

(52) U.S. Cl.

CPC .............. *A61N1/3752* (2013.01); *H02G 3/26* (2013.01); *H05K 3/4644* (2013.01); *H05K 5/0247* (2013.01); *H01L 23/49827* (2013.01); *H01L 24/48* (2013.01); *H01L 2224/48091* (2013.01); *H01L 2924/12042* (2013.01); *H01L 2924/19107* (2013.01); *Y10T 29/49126* (2015.01)

(56) References Cited

U.S. PATENT DOCUMENTS

| | | | | |
|---|---|---|---|---|
| 7,873,419 | B2 * | 1/2011 | Greenberg | A61N 1/0543 607/54 |
| 8,000,804 | B1 * | 8/2011 | Wessendorf | A61N 1/0543 607/115 |
| 8,208,270 | B2 * | 6/2012 | Mori | B23K 1/0016 361/770 |
| 8,508,947 | B2 * | 8/2013 | Ganesan | H05K 7/00 174/117 FF |
| 2002/0110344 | A1 | 8/2002 | Jin | |
| 2006/0063462 | A1 | 3/2006 | Ding et al. | |
| 2007/0107524 | A1 | 5/2007 | O'Brien et al. | |
| 2007/0221399 | A1 * | 9/2007 | Nishizawa | B32B 18/00 174/250 |

* cited by examiner

HERMETIC ELECTRONICS PACKAGE WITH DUAL-SIDED ELECTRICAL FEEDTHROUGH CONFIGURATION

CROSS-REFERENCE TO RELATED APPLICATIONS

This patent document claims the benefits and priorities of U.S. Provisional Application No. 61/496,846, tiled on Jun. 14, 2011, hereby incorporated by reference.

FEDERALLY SPONSORED RESEARCH OR DEVELOPMENT

The United States Government has rights in this invention pursuant to Contract No. DE-AC52-07NA27344 between the United States Department of Energy and Lawrence Livermore National Security, LLC for the operation of Lawrence Livermore National Laboratory.

TECHNICAL FIELD

This patent document relates to hermetically sealed electronic packages and devices, and in particular to an electronic package having electrical feedthroughs on two sides of the package for connecting to one or more external electrode arrays for high density electrode array operation.

BACKGROUND

Electrically-active implantable bio-medical devices (such as for example pacemakers, cochlear implants, and neural prosthetics) are increasing in popularity due to the potential of continuous monitoring, instantaneous and directed delivery of treatments, reduction of treatment costs, and unique treatment options. However, because many of the component materials used in such devices are not bio-compatible, that is, they are toxic to the body and can induce undesirable biological reactions, it is critical to hermetically seal the non-bio-compatible components (e.g. CMOS, passive components, batteries) in a bio-compatible material, so that the body does not have a cyto-toxic response. Hermetic sealing also helps protects electrical components from damage due to moisture and the corrosive environment in the body.

FIG. 1 shows a schematic illustration of a general approach to hermetically encapsulating implantable devices, such as 10, where non-bio-compatible components and materials 11, such as electronics, are encapsulated in a hermetically sealed package 12 made of bio-compatible materials. In this arrangement, an array of hermetic electrically conducting feedthroughs 13 is provided on an electrically insulating portion 14 of the package 12 for use as electrical conduits which allow communication of electrical signals between the body and electronics within the package.

And U.S. Pat. No. 7,881,799 describes a retinal prosthetic device having a hermetically sealed electronic package that contains a single side of the package that consists of electrical feedthroughs to transfer electrical signals between the device electronics and the polymer electrode array that attaches to the retina. One limitation of this assembly method is a restriction in the number of electrical signals that can be transmitted through the electronics package. State-of-the-art bio-compatible ceramics with electrical feedthroughs are limited in density by the inability to create closely spaced, small diameter vias that can be filled with metal paste.

In order to improve the performance of implantable devices, it is advantageous to provide electrically conductive feedthroughs which allow connection to hermetically sealed electronic devices from more than one wall of the hermetic package so as to increase feedthrough density and interactivity with the implanted medium.

SUMMARY

The technology described in this patent document includes hermetic electronics packages, devices, and systems with high-density hermetic electrical feedthroughs and methods for fabricating the same.

In one example implementation, a hermetic electronics package is provided comprising: a metal case with opposing first and second open ends; a first feedthrough construction having an electrically insulating substrate and an array of electrically conductive feedthroughs extending therethrough; a second feedthrough construction having an electrically insulating substrate and an array of electrically conductive feedthroughs extending therethrough; said electrically insulating substrates of the first and second feedthrough constructions connected to the opposing first and second open ends, respectively, of the metal case so as to form a hermetically sealed enclosure; and a set of electronic components located within the hermetically sealed enclosure and operably connected to the feedthroughs of the first and second feedthrough constructions so as to electrically communicate outside the package from opposite sides thereof.

In another example implementation, a hermetically-sealed electronics device is provided comprising: a hermetic electronics package comprising: a metal case with opposing first and second open ends; a first feedthrough construction having an electrically insulating substrate and an array of electrically conductive feedthroughs extending therethrough; a second feedthrough construction having an electrically insulating substrate and an array of electrically conductive feedthroughs extending therethrough; said electrically insulating substrates of the first and second feedthrough constructions connected to the opposing first and second open ends, respectively, of the metal case so as to form a hermetically sealed enclosure; and a set of electronic components located within the hermetically sealed enclosure and operably connected to the feedthroughs of the first and second feedthrough constructions; and an electrode array having a plurality of traces extending between electrodes at a lead end and bifurcated connector ends, wherein the electrodes at the bifurcated connecter ends are connected to the feedthroughs of the first and second feedthrough constructions no as to electrically communicate with the set of electronic components from opposite sides of the package.

And in another example implementation, a method of fabricating an hermetic electronics package is provided, comprising: bonding a first electrically insulating substrate of a first feedthrough construction having the first electrically insulating substrate and a first array of electrically conductive feedthroughs extending therethrough, to a first open end of a first metal case having opposing first and second open ends; bonding a second electrically insulating substrate of a second feedthrough construction having the second electrically insulating substrate and a second array of electrically conductive feedthroughs extending therethrough, to a first open end of a second metal case having opposing first and second open ends; fixedly connecting a set of electronic components to at least one of the first and second feedthrough constructions and electrically connecting to at least one of the first and second feedthrough arrays; and bonding the second Open ends of the first and second metal cases together so as to form a hermetically sealed enclosure containing the set of electronic components from which the set of electronic components may electrically communicate outside the package from opposite sides thereof.

These and other implementations and various features and operations are described in greater detail in the drawings, the description and the claims.

DETAILED DESCRIPTION

Figure 1:
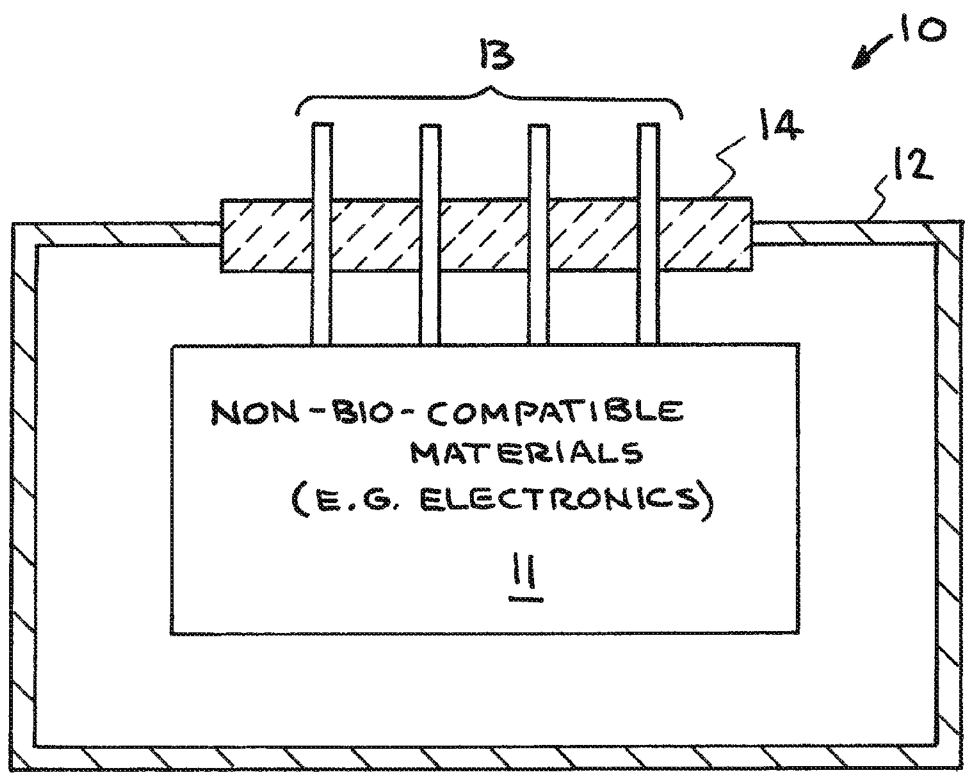
FIG. 1 is a schematic view of an implantable device illustrating a common approach to encapsulating non-bio-compatible component materials in a bio-compatible sealed package.

The present invention is generally directed to a hermetic electronic package with a dual-sided electrical feedthrough configuration that may be used for electrically active, implantable bio-medical devices. The hermetically-sealed package contains a set of electronic components (e.g. a combination of passive components, electronic chips, interconnects, antennas for power and data telemetry, cables, etc.). And a plurality of electrically conductive feedthroughs are provided on opposing walls of the package to enable electronic components housed inside to electrically communicate outside the package. In particular, a single or multiple polymer-based multi-electrode arrays (which for example may contain electrodes that interface with living tissue and cells) may be attached to the feedthroughs of the electronic package. Such a package and device can be used for, but is not limited to, retinal prostheses, neural prostheses, and a variety of implantable bio-medical devices that stimulate or record from live tissue. In this manner, the present invention addresses the problem described in the Background of enabling high density feedthrough operation and scalability by using multiple walls of the electronics package for passing electrical feedthroughs. The resulting device would exhibit the same bio-compatibility and hermeticity specifications, however it has the ability to double, or triple the number of electrical signals that can be simultaneously transmitted from the device. This enables a retinal device to equivalently increase the resolution visible to patients, which significantly improves the existing technology.

For bio-medical implant applications in particular, substrate materials that have high bio-compatibility and are capable of being hermetically sealed to implantable metal packages are preferred. Example bio-compatible electrically conductive substrate materials that may be used include: titanium and its alloys, such as surgical grade titanium—Ti6Al4V, Ti6Al4V ELI ('extra low interstitials') and niobium and alloys. While bio-compatible electrically conductive metal substrates are preferred in bio-medical implant applications, if the electrically conductive substrate material was further coated with an insulating material then any electrical conductor may be used, such as but not limited to platinum and alloys (such as platinum-iridium); iridium and alloys; ruthenium and alloys; Nitinol (Ti—Ni); palladium and alloys; rhodium and alloys, gold and alloys; copper and alloys, aluminum and alloys, surgical grade stainless steel such as 316LVM; p- or n-type doped silicon; etc. Electrical resistance of individual wires may be less than about 500 ohms. And it is also notable that various types of electrically insulating materials may be used as well, e.g. glass, polymer, or ceramic insulators. For example, the electrically insulating material may be a bio-compatible electrically insulating material, such as for example sealing glasses such as Pyrex, non-leaded glass, boro-silicate glass, glass-frit powder or paste, glasses or ceramics containing one or more of $B_2O_3$, CaO, BaO, $SiO_2$, $La_2$ $O_3$, $Al_{2O3}$, $Li_2O_3$, $Ti_{O2}$.

Figure 2:
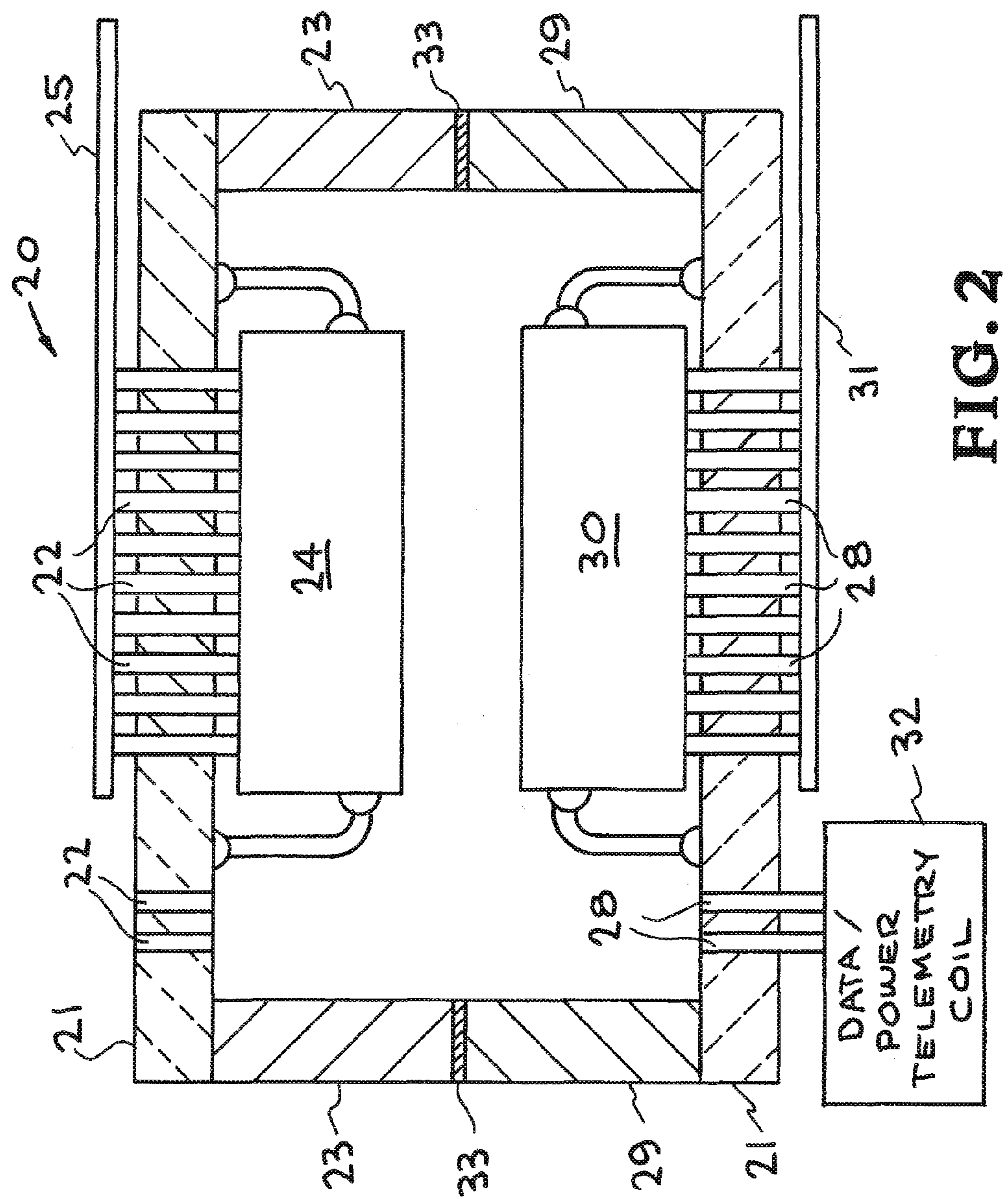
FIG. 2 is a schematic view of a first example embodiment of the hermetic electronic package of the present invention having two sides with electrical feedthroughs.

Turning now to the drawings, FIG. 2 shows a first exemplary embodiment of the hermetic electronic package and system of the present invention, generally indicated at 20. And FIGS. 3-7 show a first exemplary method of constructing/fabricating the package shown in FIG. 2. As shown in FIG. 2, the package 20 forms an enclosure formed by a metal case, which may have, for example, a cylindrical or square cross-section with opposing open ends. The metal package may be made of, but is not limited to Stainless steel, Niobium, titanium, palladium, gold, ruthenium, iridium and other bio-compatible metals. In FIG. 2, the metal case is shown comprised of two smaller metal cases 23 and 29 which are aligned and connected in an end-to-end arrangement. The connection is shown at 33, and may be produced using various methods, such as for example laser welding or brazing, or other hermetic joining method.

The metal case (i.e. the two smaller metal cases together) has one end (top end) that is capped with a first (e.g. top) electrical feedthrough construction, and an opposite end (bottom end) that is capped with a second (e.g. bottom) electrical feedthrough construction. Each of the first and second electrical feedthrough constructions have an electrically insulating substrate (21, 27), and a plurality of electrically conductive feedthroughs (22, 28) extending through it. The electrically insulating substrate may be made of for example, a ceramic with multiple metal-filled vias for the feedthroughs. And the electrically insulating substrates 21, 27 in particular are brazed (e.g. melting a braze alloy), bonded, or otherwise hermetically joined to the metal casing, so as to form the hermetically sealed enclosure which houses a set of electronic components (e.g. 24 and 30) on the inside of the device, including for example, integrated circuit chips (electronic drivers, de-multiplexers, etc), passive electrical components (resistors, capacitors, diodes, etc), interconnects (wire-bonds, electrical traces), cables, and antenna (for wireless data and power telemetry). In particular, FIG. 2 shows two subsets of electronic components 24 and 30, with subset 24 fixedly connected to the first (top) feedthrough construction and electrically connected to the associated feedthroughs, and subset 30 fixedly connected to the second (bottom) feedthrough construction and electrically connected to the associated feedthroughs. In particular, two driver/stimulator chips are shown to drive the electrical signals to the respectively top and botton feedthroughts and to the respective electrodes on the top and bottom polymer electrode arrays. And a data/power telemetry coil 32 is also shown on the exterior of the package and connected to feedthroughs of the bottom feedthrough construction. It is appreciated that electronic component assembly may involve various techniques known in the art, such as for example, thermo-compression flipchip bonding of the IC chips, conductive epoxies to attach passive components, wire-bonding, and lithographically patterned conductive traces.

Furthermore, on the outside of the package, a single or multiple polymer electrode array may be provided and connected to the feedthroughs from opposite sides of the package. In particular, FIG. 2 shows a top polymer thin film electrode array 25 connected to the feedthroughs of the top feedthrough construction, and a bottom polymer thin film electrode array 31 connected to the feedthroughs of the bottom feethrough construction. The polymer electrode array consists of a multitude of conductive traces sandwiched between multiple polymer layers. In particular, the electrode array may have a plurality of traces extending between electrodes at a lead end and a connector end. The lead end of the polymer electrode array terminates in the electrodes that interface with the implanted medium, e.g. tissue (for electrical recording or stimulation). Also, the connector end of a single polymer electrode array may be split or otherwise bifurcated to connect to the top and bottom feedthroughs of the first and second feedthrough constructions so as to electrically communicate with the set of electronic components from opposite sides of the package.

Figure 3:
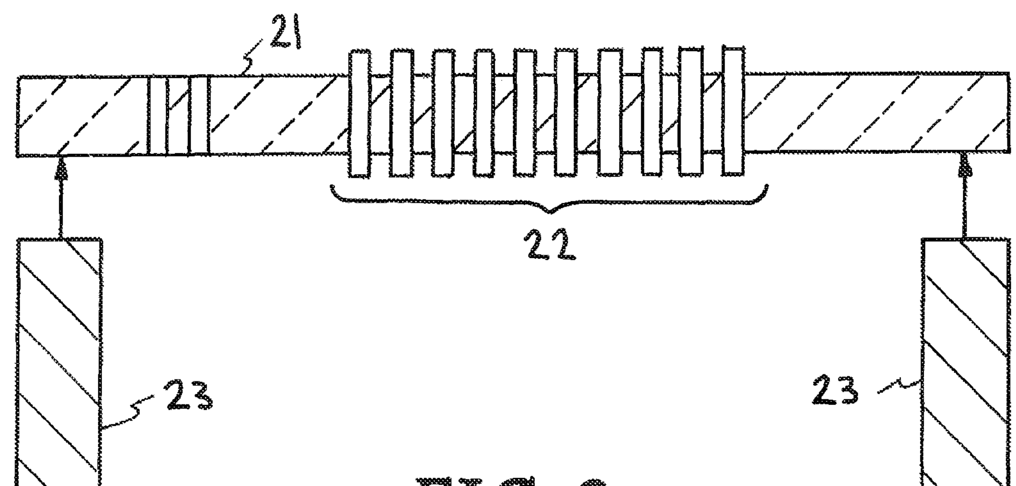
FIGS. 3 and 4 show a first exemplary step in an example method for constructing the embodiment of FIG. 2, and showing the bonding of each of the top and bottom feedthrough substrates to its respective metal casing.
Figure 4:
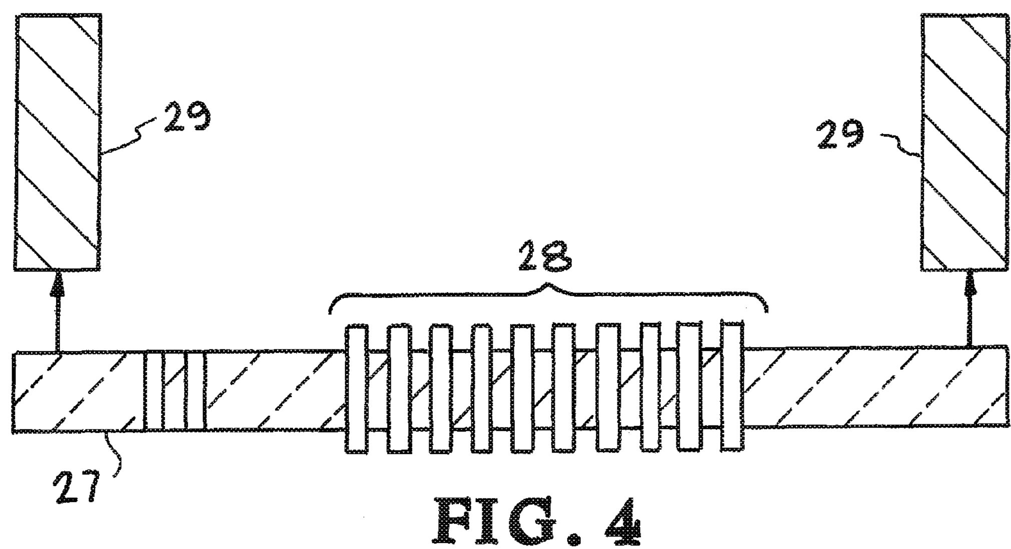
Figure 5:
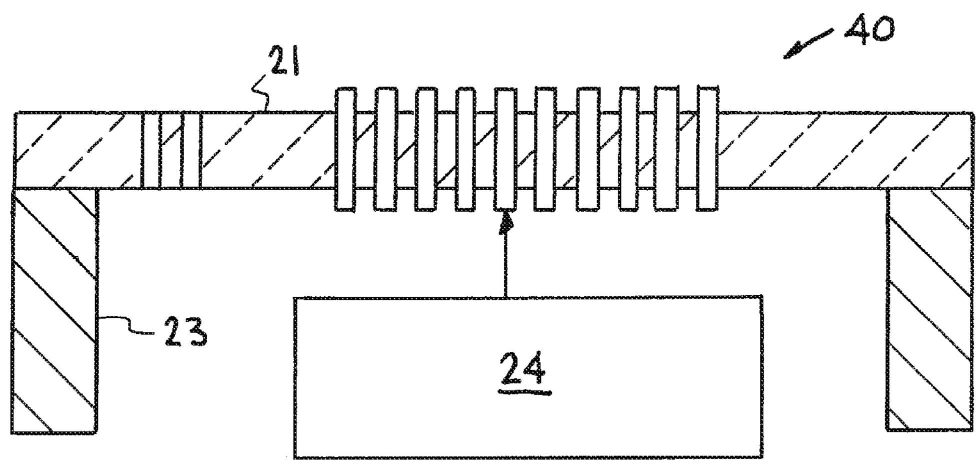
FIGS. 5 and 6 show a second exemplary step in an example method for constructing the embodiment of FIG. 2, and showing the connection of two subsets of electronic components to the top and bottom feedthrough substrates, respectively.
Figure 6:
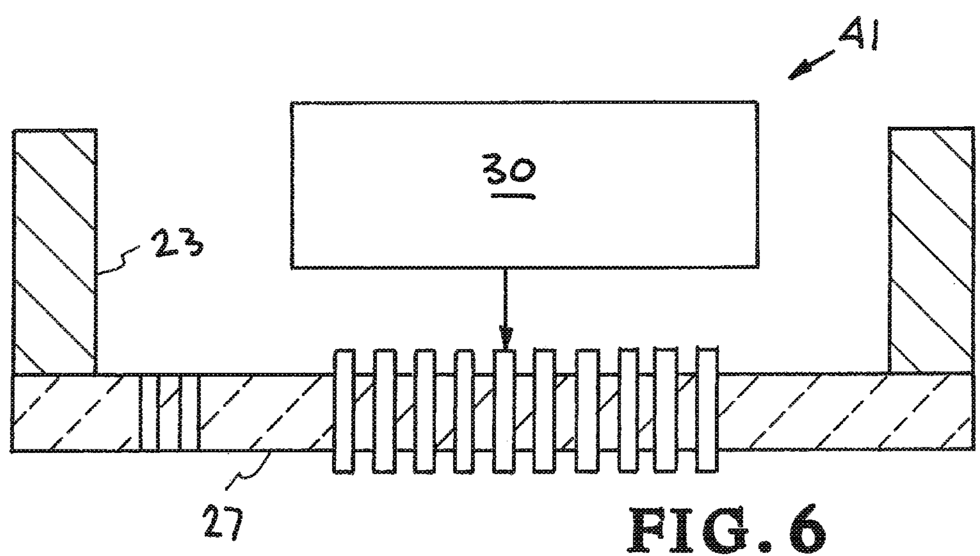
Figure 7:
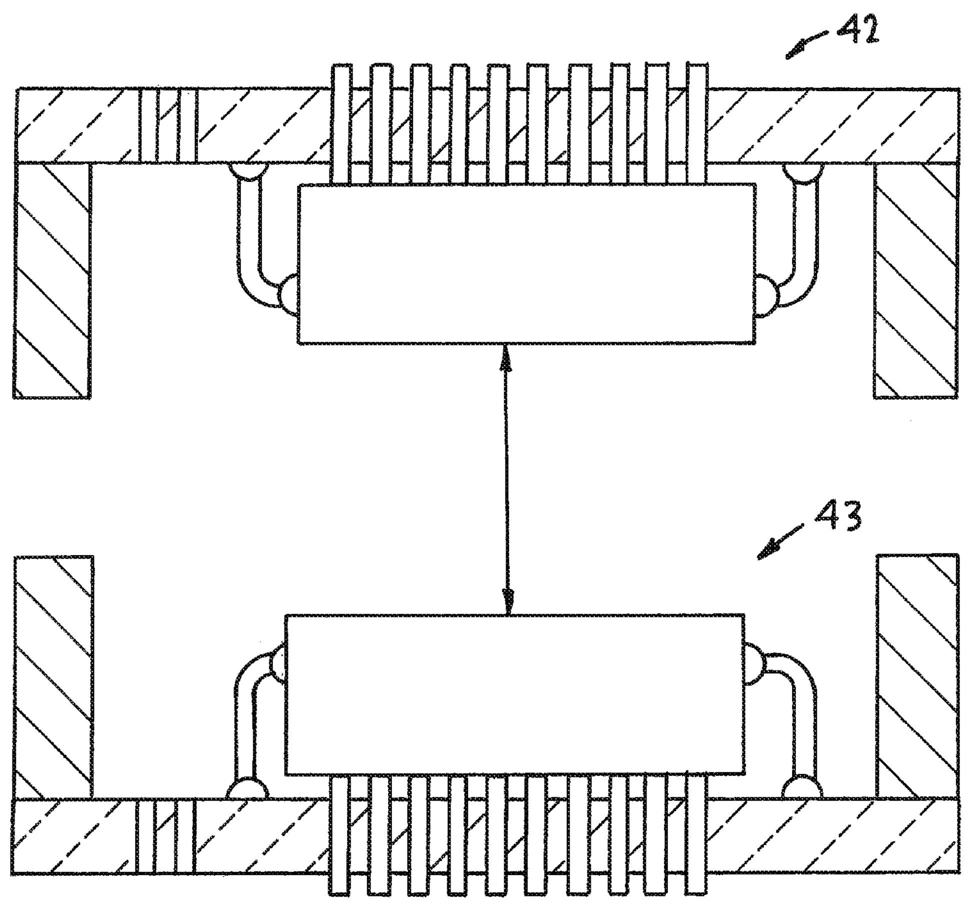
FIG. 7 shows a third exemplary step in an example method for constructing the embodiment of FIG. 2, and showing the connection of the two halves formed from FIGS. 3-6.

FIGS. 3-7 show an example fabrication method of constructing the embodiment described in FIG. 2. In particular, FIGS. 3 and 4 show a first step, where the top feedthrough substrate 21 is joined to one of the shorter metal cases 23, and the bottom feedthrough substrate 27 is separately joined to the another one of the shorter metal cases 29, as indicated by the arrows. And FIGS. 5 and 6 shows the assembly of two subsets of electronics components 24 and 30 to the respective top and bottom halve shells 40 and 41 formed as described in FIGS. 3 and 4. And finally, FIG. 7 shows the formation of the full device by joining the two completed halves 42 and 43 together, such as by laser welding or brazing, or using another hermetic joining method to attach both half-packages together.

Figure 8:
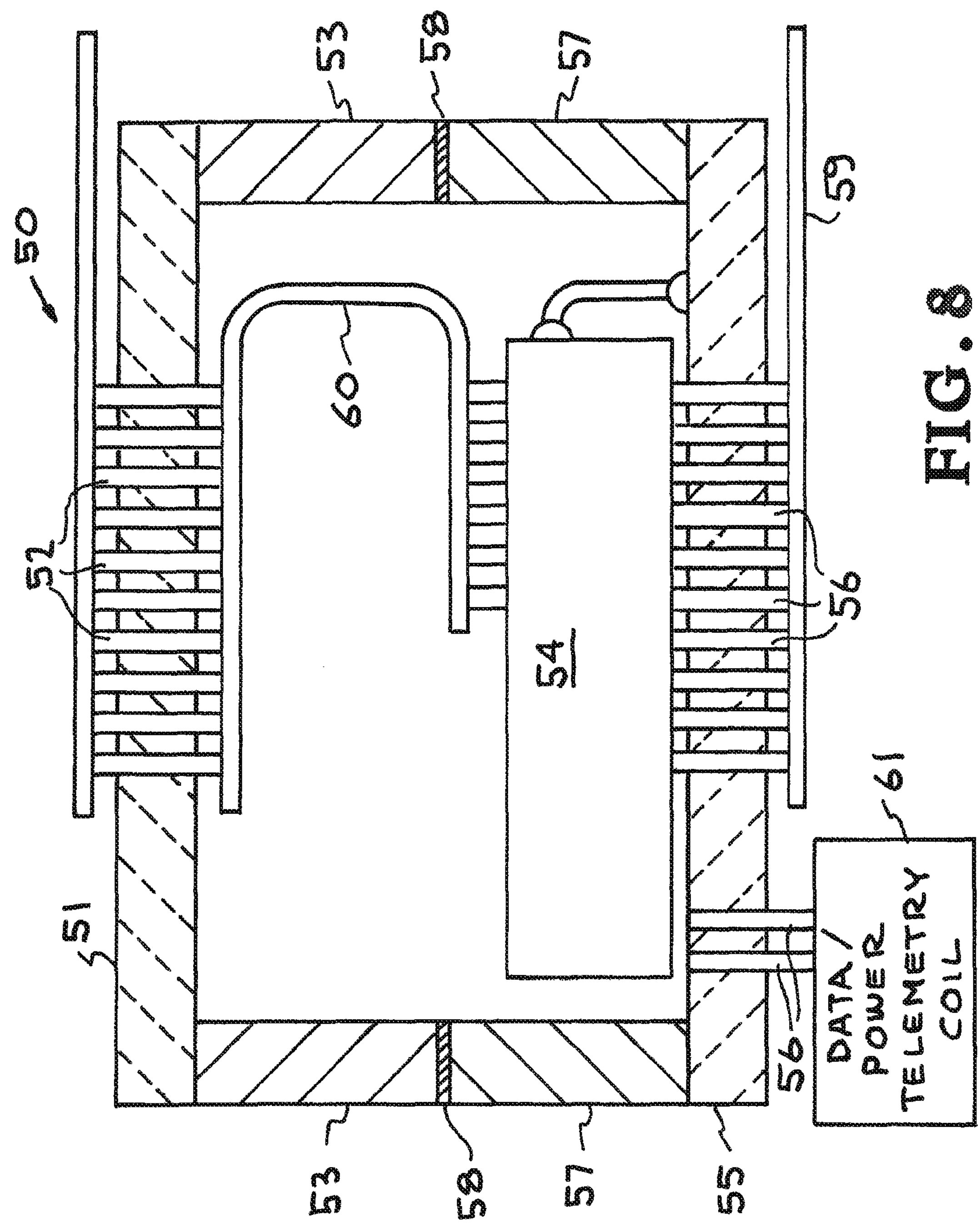
FIG. 8 is a schematic view of a second example embodiment of the hermetic electronic package of the present invention having two sides with electrical feedthroughs.

FIG. 8 shows another exemplary embodiment of the present invention, generally indicated at 50, having a single driver that is multiplexed over top and bottom feedthrough constructions. In this embodiment, a single driver (integrated circuit chip) is used to drive electrical signals to all the electrodes for both (top and bottom) polymer electrode arrays. The top and bottom electrodes are connected with a flexible polymer interconnect cable or ‘flex cable’ (multiple electrical traces sandwiched or patterned on polymer substrates). The driver chip may operate at a higher frequency than what is necessary for the performance of the device. In this case, multiple demultiplexer chips can be used to increase the number of simultaneously deliverable electrical signals to the electrodes. In particular, as shown in FIG. 8, a single subset of electronic components 54 is fixedly connected to a bottom feedthorugh substrate 55 and electrically connected to feedthroughs 56. Similar to the embodiment of FIG. 2, a top feedthrough substrate 51 having feedthroughs 52 is hermetically joined to a smaller metal case 53, and the bottom feedthrough substrate 55 is joined to another smaller metal case 57, with the two smaller metal cases joined (e.g. braze) at 58. Top and bottom electrode arrays are also shown at 59 and 59'. FIG. 8 in particular shows the use of a flexible cable 60 which connects the subset of electronic components 54 to the feedthroughs 52 of the top feedthrough construction. And a data power telemetry coil is also shown at 61.

Figure 9:
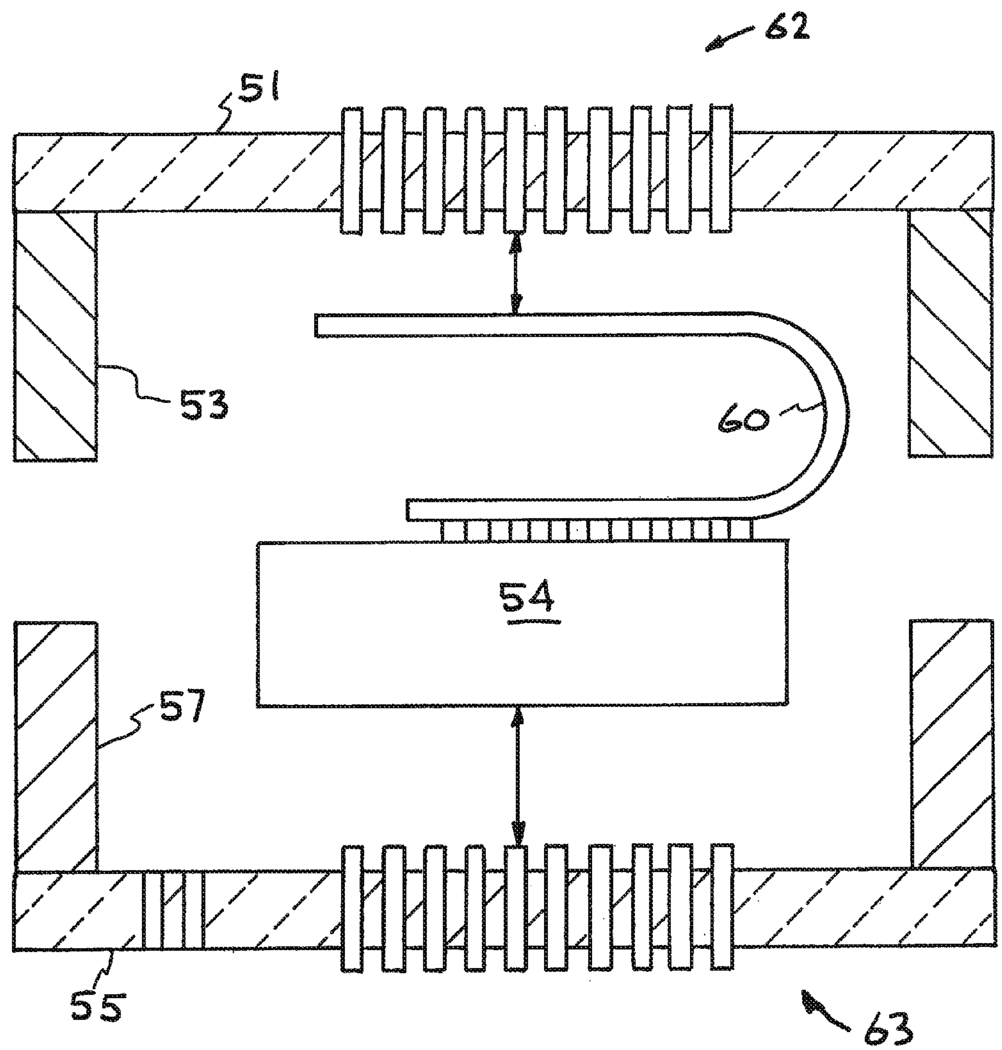
FIG. 9 shows a first exemplary step in an example method for constructing the embodiment of FIG. 8, and showing the connection of the subset of electronic components to a bottom feedthrough substrate, and a cable to the top feedthrough substrate.
Figure 10:
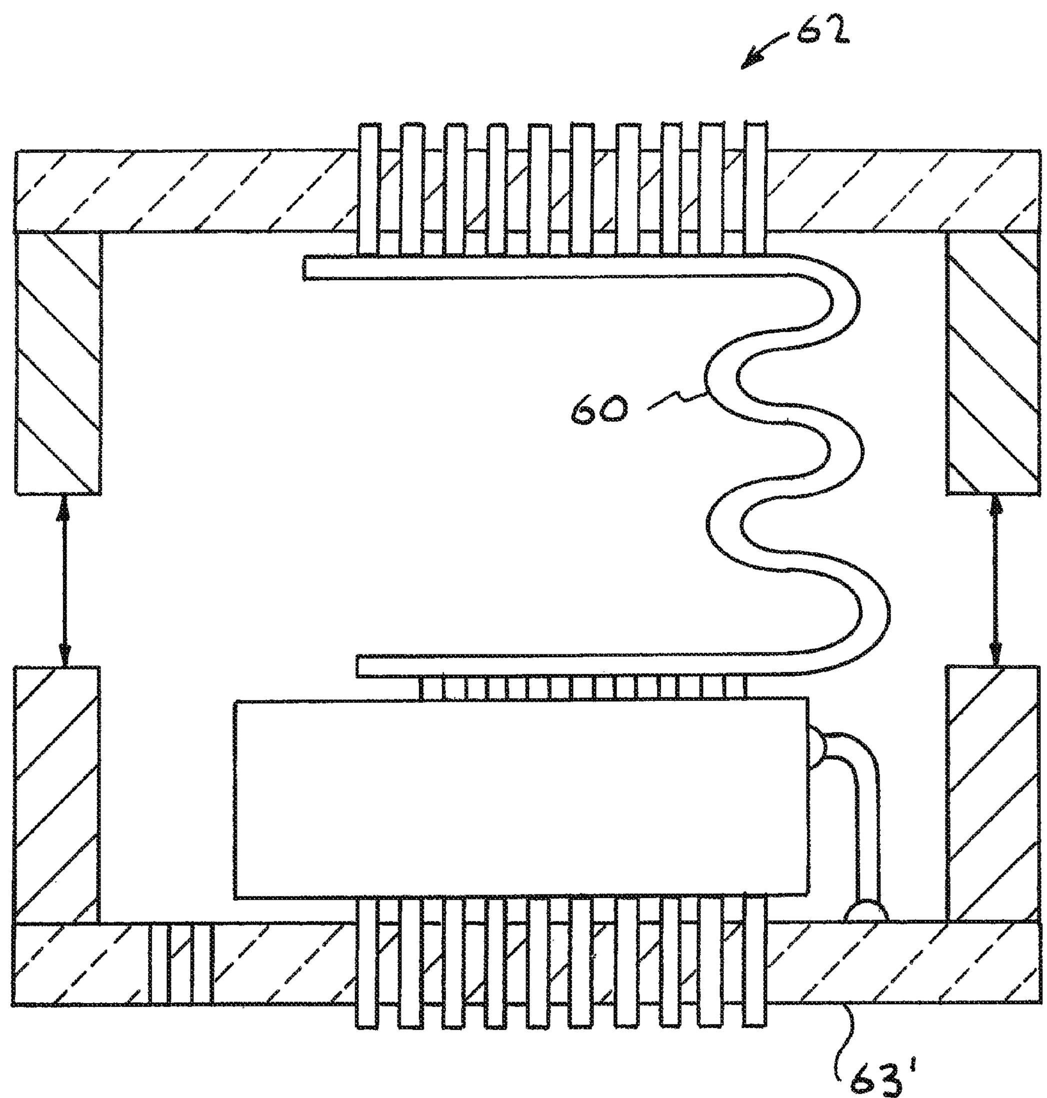
FIG. 10 shows a second exemplary step in an example method for constructing the embodiment of FIG. 8, and showing the connection of the two half shells of the package.

FIGS. 9 and 10 show one example method of construction/fabrication of the embodiment of FIG. 8. The electronic components 54 (with flexible cable 60 attached thereto) is connected to the bottom half shell construction 63 formed by joining the substrate 55 with metal case 57. And the flex cable 60 is joined to the top half shell construction 62 formed by joining the substrate 51 with metal case 53. And in FIG. 10, the two complete halves 62 and 63' are hermetically joined together.

In all of the embodiments described above, a combination of microfabrication processes is used for assembling the entire device. Hermetic feedthrough substrates—manufactured by filling vias in a ceramic substrate with gold or platinum conductors. The top and bottom surface of the ceramic are metalized and patterned using lithographic processes. The substrate is attached to the metal package using brazing. The metal package may consist of a ring and a lid, in which case they are attached using laser welding. The thin-film electrode array consists of metal layers and traces sandwiched between layers of polymer (such as silicone, polyimide and parylene). The driver chip and the de-multiplexer are fabricated using standard CMOS manufacturing methods. Passive components are purchased from volume manufacturers, and may be attached to the interconnect board or other substrates with conductive epoxies or solder. The driver chip or the de-multiplexer can be electrically connected to the other components using flip-chip bonding of conductive stud bumps, by conductive epoxy bumps, or by wirebonding between metal pads on each substrate. The microelectrode array is flip-chip bonded to the can using conductive epoxy bumps printed on both the ceramic feedthrough substrate and the microelectrode array. And Epoxies may be used after many of the above processes to provide mechanical stability, or electrical isolation.

It is notable that hermetically sealed packages with electrical feedthroughs is commonly used by many companies in the bio-medical device industry to separate non-bio-compatible components from bodily tissue. However, electrical feedthroughs are also heavily used in the semiconductor industry to interconnect electronic chips. And electrical feedthroughs may also be used in other applications, such as separating sensors or electronics from harsh environments in the field. It is appreciated therefore that while bio-compatible materials are preferred for use as one or both of the electrically conductive substrate/feedthroughs and electrically insulating materials of the present invention when used in bio-medical implant applications, other non-bio-compatible materials may be used in the alternative for other non-bio-medical applications. The challenge in all these applications, however, remains the same, that is to create very high-density hermetic feedthroughs using materials that are compatible with the environment of application.

Although the description above contains many details and specifics, these should not be construed as limiting the scope of the invention or of what may be claimed, but as merely providing illustrations of some of the presently preferred embodiments of this invention. Other implementations, enhancements and variations can be made based on what is described and illustrated in this patent document. The features of the embodiments described herein may be combined in all possible combinations of methods, apparatus, modules, systems, and computer program products. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described above should not be understood as requiring such separation in all embodiments.

Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known to those of ordinary skill in the art are expressly incorporated herein by reference and are intended to be encompassed by the present claims. Moreover, it is not necessary for a device to address each and every problem sought to be solved by the present invention, for it to be encompassed by the present claims. Furthermore, no element or component in the present disclosure is intended to be dedicated to the public regardless of whether the element or component is explicitly recited in the claims. No claim element herein is to be construed under the provisions of 35 U.S.C. 112, sixth paragraph, unless the element is expressly recited using the phrase "means for."

We claim:

1. A hermetically-sealed electronics device comprising:

a hermetic electronics package comprising: a metal case with opposing first and second open ends; a first feedthrough construction having an electrically insulating substrate and an array of electrically conductive feedthroughs extending therethrough; a second feedthrough construction having an electrically insulating substrate and an array of electrically conductive feedthroughs extending therethrough; said electrically insulating substrates of the first and second feedthrough constructions connected to the opposing first and second open ends, respectively, of the metal case so as to form a hermetically sealed enclosure; and a set of electronic components located within the hermetically sealed enclosure and operably connected to the feedthroughs of the first and second feedthrough constructions;

a first electrode array having a plurality of traces extending between electrodes at a lead end and a connector end that is connected to the feedthroughs of the first feedthrough construction to transmit electrical signals between the set of electronic components and a surrounding region adjacent the first electrode array; and a second electrode array having a plurality of traces extending between electrodes at a lead end and a connector end that is connected to the feedthroughs of the second feedthrough construction to transmit electrical signals between the set of electronic components and a surrounding region adjacent the second electrode array, whereby the first and second electrode arrays are positioned to electrically interact with said adjacent surrounding regions from opposite sides of the package.

2. The hermetically-sealed electronics device of claim 1, wherein the set of electronic components comprises a first subset fixedly connected to the first feedthrough construction and electrically connected to the feedthroughs thereof, and a second subset fixedly connected to the second feedthrough construction and electrically connected to the feedthroughs thereof.

3. The hermetically-sealed electronics device of claim 1, wherein the set of electronic components comprises a subset fixedly connected to the first feedthrough construction and electrically connected to the feedthroughs thereof, and a cable electrically connecting the subset to the feedthroughs of the second feedthrough construction.

4. The hermetically-sealed electronics device of claim 1, wherein the metal case with opposing first and second open ends comprises two shorter metal cases connected end-to-end.

5. The hermetically-sealed electronics device of claim 1, wherein the electrically conductive feedthroughs are a bio-compatible metal.

6. The hermetically-sealed electronics device of claim 5, wherein the electrically conductive bio-compatible metal is selected from the group consisting of titanium, platinum, iridium, ruthenium, niobium, palladium, gold, stainless steel, p- or n-type doped silicon, and alloys thereof.

7. The hermetically-sealed electronics device of claim 1, wherein the electrically insulating material is selected from the group consisting of glass, polymer, ceramic, and other dielectric materials.

8. The hermetically-sealed electronics device of claim 1, wherein the electrically insulating substrate is a bio-compatible material.

9. The hermetically-sealed electronics device of claim 1, wherein the electrically insulating bio-compatible material is selected from the group consisting of sealing glasses, non-leaded glass, boro-silicate glass, glass-frit powder or paste, and glasses or ceramics containing one or more of $B_2O_3$, CaO, BaO, $SiO_2$, $La_2O_3$, $Al_2O_3$, $Li_2O_3$, $TiO_2$.

10. A method of fabricating a hermetic electronics package, comprising: bonding a first electrically insulating substrate of a first feedthrough construction having the first electrically insulating substrate and a first array of electrically conductive feedthroughs extending therethrough, to a first open end of a first metal case having opposing first and second open ends; bonding a second electrically insulating substrate of a second feedthrough construction having the second electrically insulating substrate and a second array of electrically conductive feedthroughs extending therethrough, to a first open end of a second metal case having opposing first and second open ends; fixedly connecting a set of electronic components to at least one of the first and second feedthrough constructions and electrically connecting to at least one of the first and second feedthrough arrays; and bonding the second open ends of the first and second metal cases together so as to form a hermetically sealed enclosure containing the set of electronic components from which the set of electronic components may electrically communicate outside tile package from opposite sides thereof via first and second electrode arrays each having a lead end and a connector end electrically connected to a corresponding one of the first and second feedthrough arrays.

11. The method of claim 10, wherein prior to the bonding of the second open ends, the step of fixedly connecting the set of electronic components includes fixedly connecting a first subset to the first feedthrough construction and electrically connecting the first subset to the feedthroughs of the first feedthrough construction, and fixedly connecting a second subset to the second feedthrough construction and electrically connecting the second subset to the feedthroughs of the second feedthrough construction.

12. The method of claim 10, wherein prior to the bonding of the second open ends, the step of fixedly connecting the set of electronic components includes fixedly connecting a subset of electronic components to the first feedthrough construction and electrically connecting the subset to the feedthroughs of the first feedthrough construction, and electrically connecting a cable between the subset and the feedthroughs of the second feedthrough construction.

* * * * *